US007207947B2

(12) United States Patent
Koh et al.

(10) Patent No.: US 7,207,947 B2
(45) Date of Patent: Apr. 24, 2007

(54) SYSTEM AND METHOD FOR DETECTING CIRCADIAN STATES USING AN IMPLANTABLE MEDICAL DEVICE

(75) Inventors: Steve Koh, Rowland Heights, CA (US); Euljoon Park, Stevenson Ranch, CA (US)

(73) Assignee: Pacesetter, Inc., Sylmar, CA (US)

( * ) Notice: Subject to any disclaimer, the term of this patent is extended or adjusted under 35 U.S.C. 154(b) by 424 days.

(21) Appl. No.: 10/339,989

(22) Filed: Jan. 10, 2003

(65) Prior Publication Data
US 2004/0138716 A1 Jul. 15, 2004

(51) Int. Cl.
*A61B 5/08* (2006.01)
(52) U.S. Cl. .......................... 600/529; 607/17; 607/42; 600/530; 600/531; 600/532; 600/533; 600/534; 600/535; 600/536; 600/537; 600/538; 600/539; 600/540; 600/541; 600/542; 73/23.3; 488/84
(58) Field of Classification Search ............... 607/17, 607/18, 22, 42; 600/361, 322, 345, 529–542; 73/23.3; 488/84
See application file for complete search history.

(56) References Cited

U.S. PATENT DOCUMENTS

| 4,712,555 A | * | 12/1987 | Thornander et al. .......... 607/17 |
| 4,716,887 A | | 1/1988 | Konig et al. .......... 128/419 PG |
| 4,901,725 A | * | 2/1990 | Nappholz et al. .............. 607/17 |
| 5,088,488 A | * | 2/1992 | Markowitz et al. ............ 607/27 |
| 5,097,831 A | | 3/1992 | Lekholm .............. 128/419 PG |
| 5,413,592 A | | 5/1995 | Schroeppel ................... 607/18 |
| 5,476,483 A | | 12/1995 | Bornzin et al. ................ 607/17 |
| 5,487,753 A | * | 1/1996 | MacCarter et al. ............ 607/17 |
| 5,496,352 A | | 3/1996 | Renger .......................... 607/19 |
| 5,733,312 A | | 3/1998 | Schloss et al. ................ 607/17 |
| 5,836,988 A | | 11/1998 | Cooper et al. ................ 607/19 |
| 5,908,392 A | | 6/1999 | Wilson et al. .............. 600/509 |
| 6,055,454 A | | 4/2000 | Heemels ....................... 607/18 |
| 6,128,534 A | | 10/2000 | Park et al. ..................... 607/17 |
| 6,275,727 B1 | | 8/2001 | Hopper et al. .............. 600/513 |
| 6,336,048 B1 | * | 1/2002 | Bonnet ......................... 607/19 |
| 6,459,929 B1 | | 10/2002 | Hopper et al. .............. 600/513 |
| 6,589,188 B1 | * | 7/2003 | Street et al. ................ 600/538 |
| 6,600,949 B1 | * | 7/2003 | Turcott ......................... 600/518 |
| 6,731,984 B2 | * | 5/2004 | Cho et al. ..................... 607/17 |

(Continued)

FOREIGN PATENT DOCUMENTS

EP 1151719 A2 11/2001

(Continued)

*Primary Examiner*—Robert E. Pezzuto
*Assistant Examiner*—Deborah Malamud

(57) ABSTRACT

Techniques are provided for detecting the circadian state of a patient using an implantable medical device based on selected blood carbon dioxide ($CO_2$) parameters. In one example, the implantable device tracks changes in end tidal $CO_2$ ($etCO_2$) levels and changes in maximum variations of $pCO_2$ levels per breathing cycle ($\Delta_{cycle}CO_2$) over the course of the day and determines the circadian state based thereon. It has been found that average $etCO_2$ levels are generally highest and average $\Delta_{cycle}CO_2$ levels are generally lowest while a patient is asleep and opposite while a patient is awake. Hence, by tracking changes in average $etCO_2$ and $\Delta_{cycle}CO_2$ levels over the course of the day, circadian states can be detected. Minute ventilation and activity levels are used to assist in the determination of the circadian state. Additional techniques are directed to detecting the stage of sleep.

10 Claims, 11 Drawing Sheets

U.S. PATENT DOCUMENTS

| | | |
|---|---|---|
| 6,904,320 B2 * | 6/2005 | Park et al. .................... 607/17 |
| 2002/0052632 A1 | 5/2002 | Ben-Haim et al. ............. 607/6 |
| 2002/0193697 A1 * | 12/2002 | Cho et al. ................... 600/529 |
| 2002/0193839 A1 | 12/2002 | Cho et al. .................... 607/17 |
| 2003/0153953 A1 | 8/2003 | Park et al. .................... 607/17 |
| 2004/0002741 A1 | 1/2004 | Weinberg .................... 607/17 |

FOREIGN PATENT DOCUMENTS

| WO | WO 01/32260 A1 | 5/2001 |
|---|---|---|

\* cited by examiner

SYSTEM AND METHOD FOR DETECTING CIRCADIAN STATES USING AN IMPLANTABLE MEDICAL DEVICE

FIELD OF THE INVENTION

The invention relates generally to implantable medical devices, such as pacemakers or implantable cardioverter/defibrillators (ICDs), and in particular to techniques for detecting circadian states (i.e. sleep/wake states) using an implantable medical device.

BACKGROUND OF THE INVENTION

A pacemaker is a medical device for implant within a patient, which recognizes various arrhythmias such as an abnormally slow heart rate (bradycardia) or an abnormally fast heart rate (tachycardia) and delivers electrical pacing pulses to the heart in an effort to remedy the arrhythmias. An ICD is a device, also implantable into a patient, which additionally or alternatively recognizes atrial fibrillation (AF) or ventricular fibrillation (VF) and delivers electrical shocks to terminate fibrillation.

Pacemakers and ICDs are often provided with the capability to detect the circadian state of the patient, i.e. whether the patient is awake or asleep, and to adjust pacing parameters based on the circadian state. For example, a base pacing rate may be reduced while the patient is asleep then increased while the patient is awake. Conventionally, circadian state is detected based on time of day using an on-board clock or detected using a posture sensor. Typically, with an on-board clock, the patient is simply deemed to be awake during the day and during the evening but asleep at night. With a posture sensor, typically, the patient is deemed to be asleep while lying down. Neither technique is particularly effective. An on-board clock does not properly allow for a reduction in pacing rates if the patient sleep during the day or for an increase in pacing rates if the patient is awake at night. Posture detection does not properly distinguish between simply lying down rather than sleeping.

More sophisticated circadian state detection techniques have been developed that exploit patient activity levels detected using an activity sensor or that exploit minute ventilation detected using a thoracic impedance detector. A detailed description of an activity sensor for use in detecting circadian states is provided in U.S. Pat. No. 5,476,483, to Bomzin et al., entitled "System and Method for Modulating the Base Rate During Sleep for a Rate-responsive Cardiac Pacemaker", which is incorporated herein by reference. Briefly, Bornzin et al. teaches the use of "activity variance" to determine if the patient is awake or sleeping. That is, an activity sensor has significantly less variability during sleep. Details of a system for exploiting minute ventilation in the detection of circadian states is set forth in U.S. Pat. No. 6,128,534 to Park et al., entitled "Implantable Cardiac Stimulation Device And Method For Varying Pacing Parameters To Mimic Circadian Cycles ", which is also incorporated by reference herein.

By using activity variance or minute ventilation, many of the problems associated with conventional circadian state detection techniques are overcome. However, room for improvement remains. In particular, minute ventilation and activity-based detection techniques can be adversely affected by frequent movement of the patient while asleep, as can occur with patients who are restless sleepers or with patients with labored breathing while asleep. Congestive heart failure (CHF) patients suffering from severe Cheyne-Stokes respiration often have quite labored breathing while asleep causing both elevated minute ventilation levels and activity levels. Hence, techniques relying only on minute ventilation and/or activity levels can erroneously conclude the patient is awake instead of asleep.

Accordingly, it would be desirable to provide an improved technique for detecting circadian states and it is to this end that aspects of the invention are generally directed. In particular, the invention is generally directed to exploiting blood carbon dioxide ($CO_2$) parameters either alone or in combination with minute ventilation and activity levels for detecting circadian states. In this regard, it has been found that patients can tolerate a higher partial pressure of $CO_2$ ($pCO_2$) in the blood stream while asleep than while awake. Hence, average $pCO_2$ levels are generally higher, on the average, while asleep than while awake. Although still higher levels can be achieved while exercising, patients with pacemakers or ICDs typically do not exercise often enough to elevate average waking $pCO_2$ levels above average sleeping $pCO_2$ levels. Moreover, it is the increasing concentration of $pCO_2$ in the blood stream during the end tidal phase of the breathing cycle (also referred to herein as $etCO_2$) that ultimately triggers inhalation. Since patients tolerate a higher concentration of $pCO_2$ in the blood stream while asleep, $etCO_2$ is slightly higher, again on the average, while sleep than while awake. In addition, it has been found that, on the average, the difference between the minimum and maximum $pCO_2$ concentrations within individual breathing cycles (referred to herein as $\Delta_{cycle}CO_2$) is greater while awake than while asleep. Hence, these and other blood $CO_2$-based parameters can be used to distinguish between sleeping and waking states, i.e. to detect circadian states, so that pacing control parameters can be adjusted accordingly.

At least one technique has been developed for detecting blood $CO_2$ levels using an implanted device. See U.S. Pat. No. 4,716,887 to Konig et al., entitled "Apparatus and Method for Adjusting Heart/Pacer Rate Relative to Cardiac PCO2 to Obtain a Required Cardiac Output". With the technique of Konig et al., average $pCO_2$ levels are detected and used in the adjustment of rate-responsive pacing rates under the assumption that higher $pCO_2$ levels generally correspond to a higher exercise states, thus requiring higher pacing rates. In other words, the technique detects changes in $pCO_2$ with time ($\Delta pCO_2$) and adjusts pacing rates based on $\Delta pCO_2$. Although the assumption that higher $pCO_2$ levels generally correspond to a higher exercise states may be true while a patient is awake, this does not recognize the fact that average $pCO_2$ levels are actually higher while asleep than while awake, at least for typical patients having pacemakers and ICDs. In any case, Konig et al. does not provide for the detection of circadian states based on blood $CO_2$ parameters but only for rate responsive pacing.

SUMMARY

In accordance with one illustrative embodiment, a technique is provided for use with an implantable medical device for detecting the circadian state of the patient. The circadian state of the patient in which the device is implanted is detected by first detecting changes in selected blood $CO_2$ parameters and then determining the circadian state of the patient based upon the changes in the selected blood $CO_2$ parameters. Preferably, a $pH/CO_2$ sensor is used to track changes in $etCO_2$ levels as well as changes in $\Delta_{cycle}CO_2$. As noted above, it has been found that average $etCO_2$ levels are generally higher and average $\Delta_{cycle}CO_2$ levels are generally lower while a patient is asleep than while awake. Hence, by tracking changes in etCO$_2$ and $\Delta_{cycle}$CO$_2$ over the course of the day, circadian states can be detected. Alternatively, corresponding blood pH levels are tracked.

In an exemplary embodiment, wherein the implantable device is a pacemaker or ICD, various control parameters of the device are automatically adjusted based on the detected circadian state. For example, the device may be programmed to switch from a normal base pacing rate to a sleep base pacing rate when the patient falls asleep. Preferably, in addition to etCO$_2$ and $\Delta_{cycle}$CO$_2$, the implantable device also tracks minute ventilation using a thoracic impedance sensor and tracks activity levels using an accelerometer. Minute ventilation and activity levels are used to assist in the determination of the circadian state. However, by primarily basing the determination of circadian state on pCO$_2$ levels, the problems noted above that may arise when using only minute ventilation and/or activity levels are substantially avoided and a more reliable determination of the circadian state is achieved.

Thus, various techniques are provided for detecting circadian states of a patient using an implantable device. Additional techniques are provided for determining the circadian state and/or the stage of sleep based on the ratio of minute ventilation to pCO$_2$. Other objects, features and advantages of the invention will be apparent from the detailed description to follow.

BRIEF DESCRIPTION OF THE DRAWINGS

The above and further features, advantages and benefits of the present invention will be apparent upon consideration of the present description taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Stimulation Device

Figure 1:
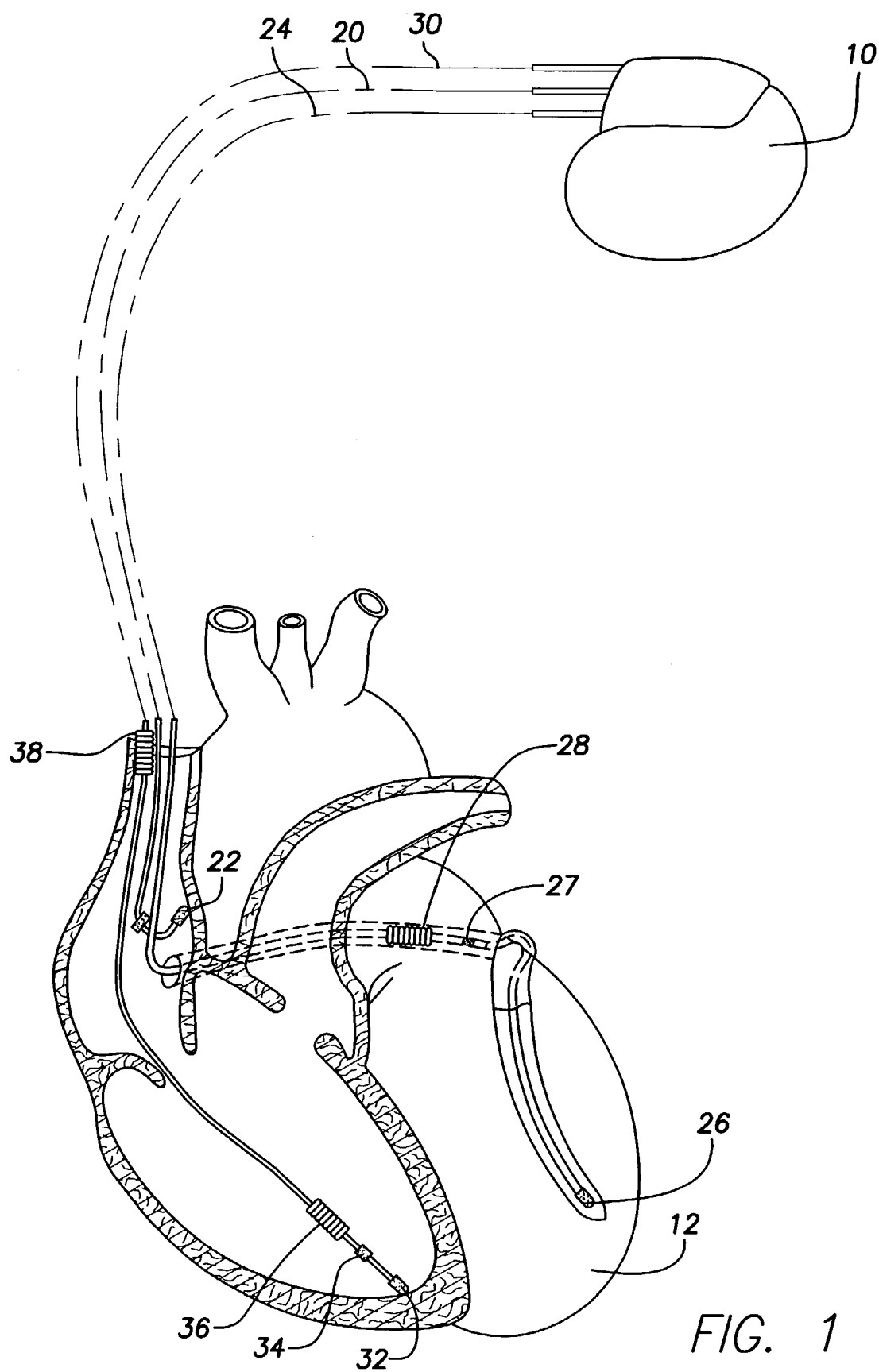
FIG. 1 is a simplified, partly cutaway view illustrating an implantable stimulation device in electrical communication with at least three leads implanted into a patient heart for delivering multi-chamber stimulation and shock therapy.

FIG. 1 illustrates a stimulation device 10 in electrical communication with a patient's heart 12 by way of three leads 20, 24 and suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left-chamber pacing therapy, the stimulation device 10 is coupled to a "coronary sinus" lead 24 designed for placement in the "coronary sinus region" via the coronary sinus os so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, the coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
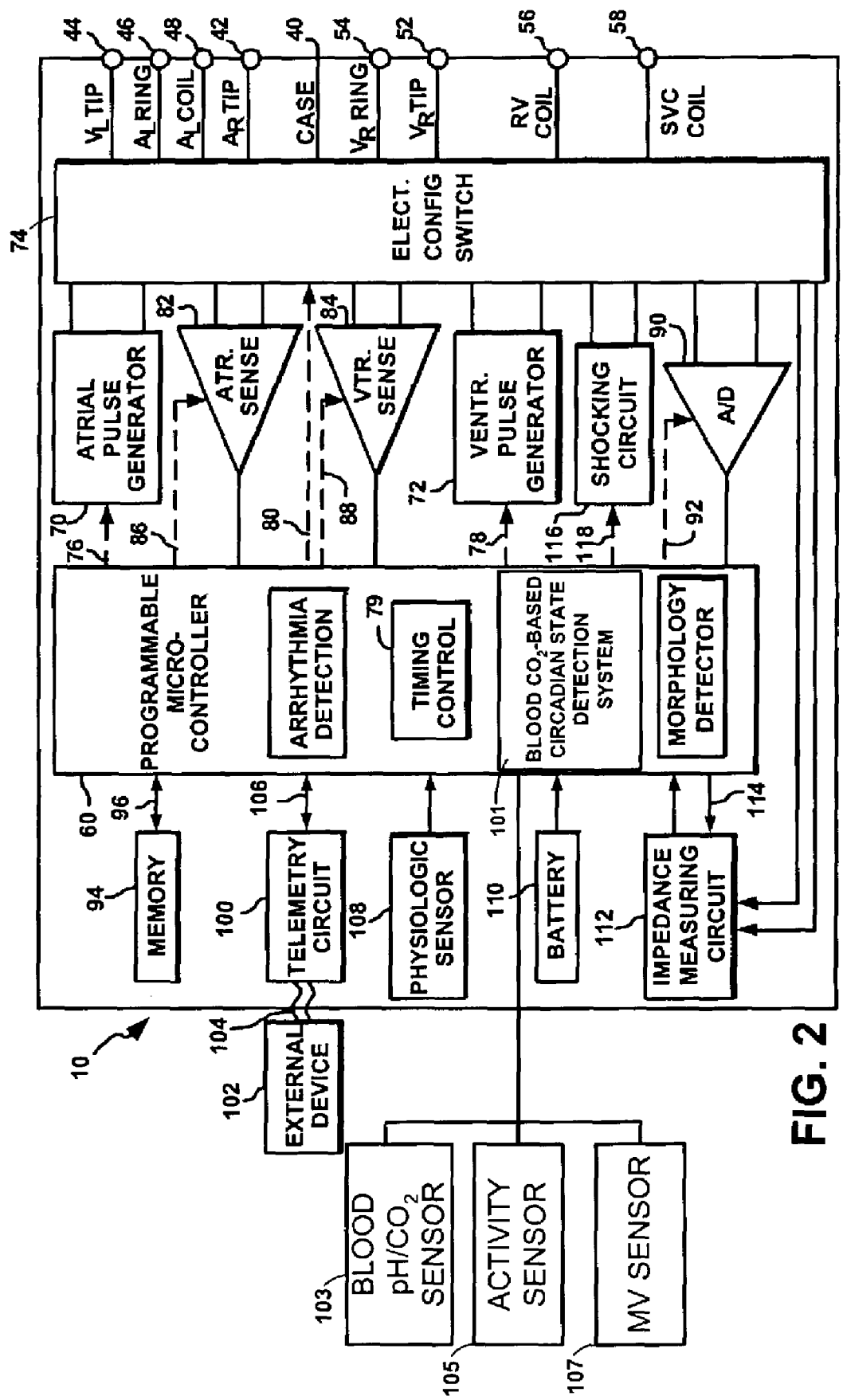
FIG. 2 is a functional block diagram of the multi-chamber implantable stimulation device of FIG. 1, illustrating the basic elements that provide cardioversion, defibrillation and/or pacing stimulation in four chambers of the heart and particularly illustrating a blood CO$_2$-based circadian state detection system for automatically detecting the circadian state of the patient.

FIG. 2 illustrates a simplified block diagram of the multi-chamber implantable stimulation device 10 which is capable of treating both fast and slow arrhythmias with stimulation therapy, including cardioversion, defibrillation, and pacing stimulation. While a particular multi-chamber device is shown, this is for illustration purposes only and one of skill in the art could readily duplicate, eliminate or disable the appropriate circuitry in any desired combination to provide a device capable of treating the appropriate chamber(s) with cardioversion, defibrillation and/or pacing stimulation.

The stimulation device 10 includes a housing 40 which is often referred to as a "can", "case" or "case electrode", and which may be programmably selected to act as the return electrode for all "unipolar" modes. The housing 40 may further be used as a return electrode alone or in combination with one or more of the coil electrodes 28, 36 or 38, for shocking purposes. The housing 40 further includes a connector (not shown) having a plurality of terminals, 42, 44, 46, 48, 52, 54, 56 and 58 (shown schematically and, for convenience, the names of the electrodes to which they are connected are shown next to the terminals). As such, to achieve right atrial sensing and pacing, the connector includes at least a right atrial tip terminal 42 adapted for connection to the right atrial (A$_R$) tip electrode 22.

To achieve left chamber sensing, pacing and/or shocking, the connector includes at least a left ventricular (V$_L$) tip terminal 44, a left atrial (A$_L$) ring terminal 46, and a left atrial (A$_L$) shocking terminal (coil) 48, which are adapted for connection to the left ventricular tip electrode 26, the left atrial ring electrode 27, and the left atrial coil electrode 28, respectively.

To support right chamber sensing, pacing and/or shocking, the connector further includes a right ventricular (V$_R$) tip terminal 52, a right ventricular (V$_R$) ring terminal 54, a right ventricular (RV) shocking terminal (coil) 56, and an SVC shocking terminal (coil) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. As is well known in the art, the microcontroller 60 typically includes a microprocessor, or equivalent control circuitry or processor, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions is well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via a switch bank 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, ventricular interconduction (V—V) delay, pacing mode, etc.), as well as to keep track of the timing of refractory periods, PVARP intervals, noise detection windows, evoked response windows, alert intervals, marker channel timing, etc.

The switch bank 74 includes a plurality of switches for connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch bank 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch bank 74 determines the "sensing polarity" of the cardiac signal by selectively closing the appropriate switches. In this way, the clinician may program the sensing polarity independent of the stimulation polarity.

Each of the sensing circuits, 82 and 84, preferably employ one or more low power, precision amplifiers with programmable gain and/or automatic gain control, bandpass filtering, and a threshold detection circuit, to selectively sense the cardiac signal of interest. The automatic gain control enables the stimulation device 10 to deal effectively with the difficult problem of sensing the low amplitude signal characteristics of atrial or ventricular fibrillation.

The outputs of the atrial and ventricular sensing circuits 82 and 84 are connected to the microcontroller 60 for triggering or inhibiting the atrial and ventricular pulse generators 70 and 72, respectively, in a demand fashion, in response to the absence or presence of cardiac activity, respectively, in the appropriate chambers of the heart. The atrial and ventricular sensing circuits 82 and 84, in turn, receive control signals over signal lines 86 and 88 from the microcontroller 60, for controlling the gain, threshold, polarization charge removal circuitry (not shown), and the timing of any blocking circuitry (not shown) coupled to the inputs of the atrial and ventricular sensing circuits 82 and 84.

For arrhythmia detection, the stimulation device 10 utilizes the atrial and ventricular sensing circuits 82 and 84 to sense cardiac signals, for determining whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into digital signals and store the digital signals for later processing and/or telemetric transmission to an external device 102.

The data acquisition system 90 is coupled to the right atrial lead 20, the coronary sinus lead 24, and the right ventricular lead 30 through the switch bank 74 to sample cardiac signals across any pair of desired electrodes.

Advantageously, the data acquisition system 90 may be coupled to the microcontroller 60 or other detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing circuitry within the microcontroller 60, and enabling the data acquisition system 90 via control signal 92 to sample the cardiac signal that falls in the capture detection window and, based on the amplitude of the sampled cardiac signal, determines if capture has occurred.

The microcontroller 60 is further coupled to a memory 94 by a suitable data/address bus 96, where the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, pacing mode, and the amplitude, waveshape and vector of each shocking pulse to be delivered to the patient's heart 12 within each respective tier of therapy. A feature of the stimulation device 10 is the ability to sense and store a relatively large amount of data (e.g., from the data acquisition system 90), which data may then be used for subsequent analysis to guide the programming of the stimulation device 10.

Advantageously, the operating parameters of the stimulation device 10 may be non-invasively programmed into the memory 94 through a telemetry circuit 100 in telemetric communication with the external device 102, such as a programmer, transtelephonic transceiver or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through an established communication link 104.

The microcontroller includes a $CO_2$-based circadian state detection system 101 detecting the current circadian state of the patient and for controlling to operations of the pacemaker based thereon. Briefly, the circadian state detection system detects the circadian state based upon a combination of end tidal $pCO_2$ levels, $\Delta_{cycle}CO_2$ levels, minute ventilation levels and activity levels. To detect $pCO_2$ levels, the device uses a blood pH/$CO_2$ sensor 103, which derives $pCO_2$ levels from blood pH. Activity level and minute ventilation are detected using, respectively, an activity sensor 105 and a minute ventilation sensor 107. The activity sensor detects activity using any variety of techniques such as analyzing accelerometer signals. Furthermore, activity signals may be processed to generate an activity variance value in accordance with the techniques described in the aforementioned Bornzin et al. and Park et al. patents. The device may also include an additional physiologic sensor denoted 108 for detecting changes in cardiac output or changes in the physiological condition of the heart. The microcontroller 60 responds to signals received from the various sensors and from the circadian state detection system by adjusting various pacing parameters (such as base rate, pacing rate, AV Delay, V—V Delay, etc.) with which the atrial and ventricular pulse generators, 70 and 72, generate stimulation pulses. Although sensors 103,105 and 107 are shown as being external to the device, depending upon the implementations, all or some of the components of the sensors may be internal to the device.

For a description of a blood pH sensor for detecting $pCO_2$ levels, see the aforementioned Konig et al patent. A minute ventilation sensor is described in U.S. Pat. No. 5,836,988 to Cooper, et al., Details regarding an exemplary activity sensor are provided in U.S. Pat. No. 5,496,352 to Renger. As noted, descriptions of activity variance sensors are provided in the Bomzin et al. and Park et al. patents. Each of these patents is incorporated by reference herein.

The operation of the circadian state detection system is described in detail below with reference to FIGS. 3–9.

The stimulation device 10 additionally includes a power source such as a battery 110 that provides operating power to all the circuits shown in FIG. 2. For the stimulation device 10, which employs shocking therapy, the battery 110 must be capable of operating at low current drains for long periods of time and also be capable of providing high-current pulses (for capacitor charging) when the patient requires a shock pulse. The battery 110 must preferably have a predictable discharge characteristic so that elective replacement time can be detected. Accordingly, the stimulation device 10 can employ lithium/silver vanadium oxide batteries.

The stimulation device 10 further includes a magnet detection circuitry (not shown), coupled to the microcontroller 60. The purpose of the magnet detection circuitry is to detect when a magnet is placed over the stimulation device 10, which magnet may be used by a clinician to perform various test functions of the stimulation device 10 and/or to signal the microcontroller 60 that an external programmer 102 is in place to receive or transmit data to the microcontroller 60 through the telemetry circuit 100.

As further shown in FIG. 2, the stimulation device 10 is shown as having an impedance measuring circuit 112 which is enabled by the microcontroller 60 via a control signal 114. Certain applications for an impedance measuring circuit 112 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of the valves, etc. The impedance measuring circuit 112 is advantageously coupled to the switch bank 74 so that any desired electrode may be used.

It is a primary function of the stimulation device 10 to operate as an implantable cardioverter/defibrillator (ICD) device. That is, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high (11–40 joules) energy, as controlled by the microcontroller 60. Such shocking pulses are applied to the patient's heart through at least two shocking electrodes, as shown in this embodiment, selected from the left atrial coil electrode 28, the RV coil electrode 36, and/or the SVC coil electrode 38 (FIG. 1). As noted above, the housing 40 may act as an active electrode in combination with the RV electrode 36, or as part of a split electrical vector using the SVC coil electrode 38 or the left atrial coil electrode 28 (e.g., using the RV electrode as a common electrode).

Cardioversion shocks are generally considered to be of low to moderate energy level (so as to minimize pain felt by the patient), and/or synchronized with an R-wave, and/or pertaining to the treatment of tachycardia. Defibrillation shocks are generally of moderate to high energy level (i.e., corresponding to thresholds in the range of 5–40 joules), delivered asynchronously (since R-waves may be too disorganized) and pertaining exclusively to the treatment of fibrillation. Accordingly, the microcontroller 60 is capable of controlling the synchronous or asynchronous delivery of the shocking pulses.

In the remaining figures, flow charts are provided for illustrating the operation and novel features of various exemplary embodiments of the invention. In the flow chart, various algorithmic steps are summarized in individual "blocks". Such blocks describe specific actions or decisions to be made or carried out as the algorithm proceeds. Where a microcontroller (or equivalent) is employed, the flow charts presented herein provide the basis for a "control program" that may be used by such a microcontroller (or equivalent) to effectuate the desired control of the device. Those skilled in the art may readily write such a control program based on the flow charts and other descriptions presented herein.

Determination of Circadian State

Figure 3:
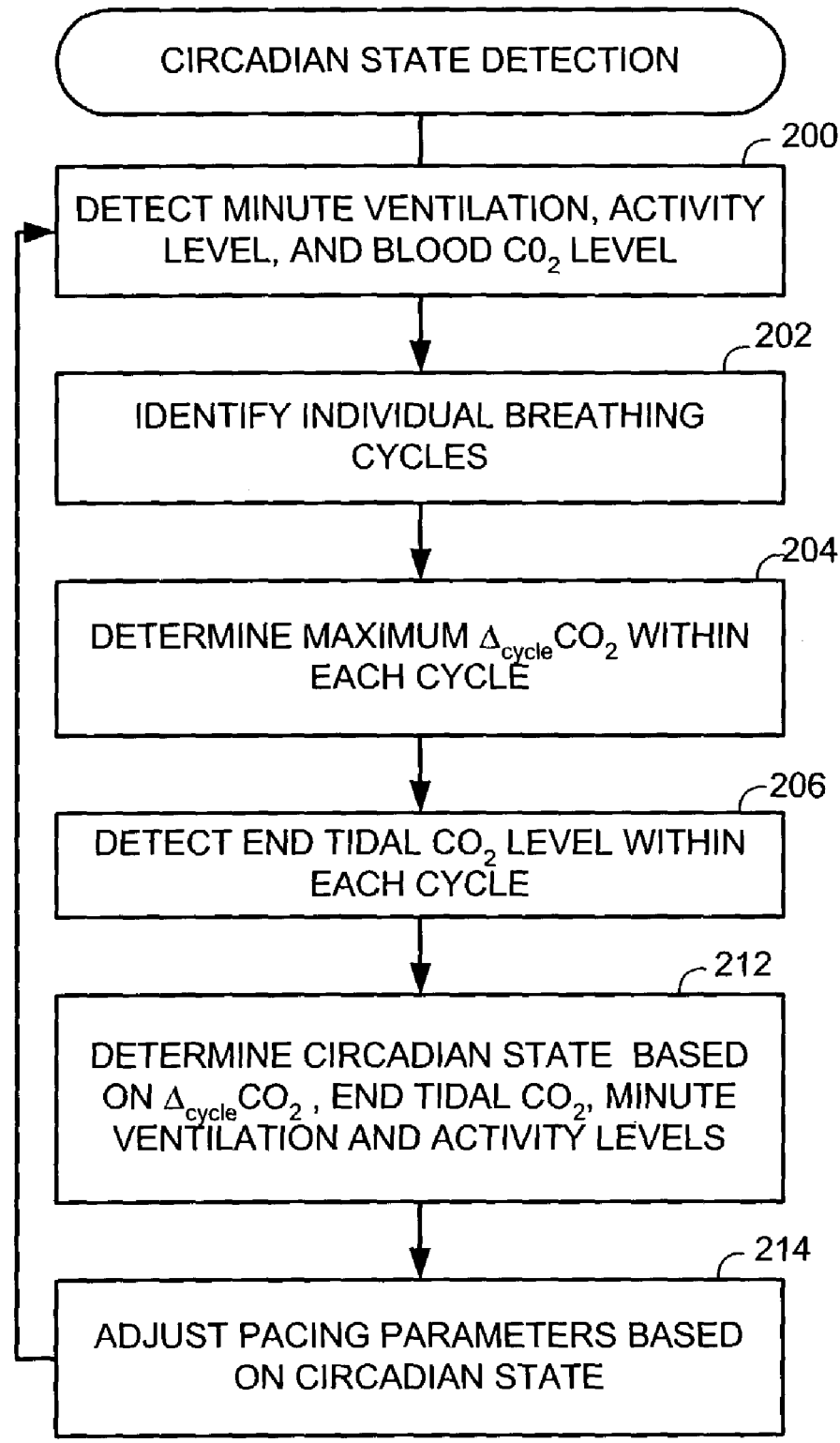
FIG. 3 is a flow diagram illustrating a method performed by the circadian state detection system of FIG. 2 to determine circadian states.

Referring now to FIG. 3, the operation of the circadian state detection system of 101 of FIG. 2 will be described. Beginning at step 200, the detection system inputs signals from the pH/CO$_2$ sensor, the activity sensor and the minute ventilation sensor (sensors 103, 105 and 107 of FIG. 2, respectively.) The pH/CO$_2$ sensor converts detected blood pH levels into signals representative of pCO$_2$ levels before forwarding the information to the circadian state detection system, which detects the circadian state based, in part, on changes in pCO$_2$ levels. In the alternative, the pH/CO$_2$ sensor instead forwards signals representative of blood pH levels directly to the circadian state detection system, which detects the circadian state based on changes in blood pH levels. In the following, the invention is described with respect to the embodiment wherein blood pH levels are converted to pCO$_2$ levels before further processing. Detection of the circadian state directly using pH levels is essentially the same as set forth in the following descriptions but modified to reflect the fact that pH levels are numerically lower when pCO$_2$ levels are numerically higher and vice versa. This is simply because higher acidity is represented by a numerically lower pH. Since higher pCO$_2$ levels make the blood more acidic, the blood pH level is thereby numerically lower.

In any case, at step 202, the detection system identifies individual breathing cycles based in changes in pCO$_2$ levels. In this regard, pCO$_2$ varies from a maximum to a minimum during a single breathing cycle. Hence, a single breathing cycle can be detected by identifying consecutive peak maxima or minima in the pCO2 signals. Alternatively, breathing cycles can be detected based on an analysis of minute ventilation signals. At step 204, the detection system then determines the maximum variation in the pCO$_2$ level within the latest breathing cycle, referred to herein as $\Delta_{cycle}CO_2$. (Note that $\Delta_{cycle}CO_2$ differs from $\Delta CO_2$, which instead refers to a change in average pCO$_2$ levels from one period of time to another.) If pH levels are instead directly processed, then the detection system determines the maximum variation in the blood pH level within the latest breathing cycle, referred to herein as $\Delta_{cycle}pH$. In any case, at step 206, the detection system also determines the etCO$_2$ level (or end tidal pH level) within each breathing cycle.

Figure 4:
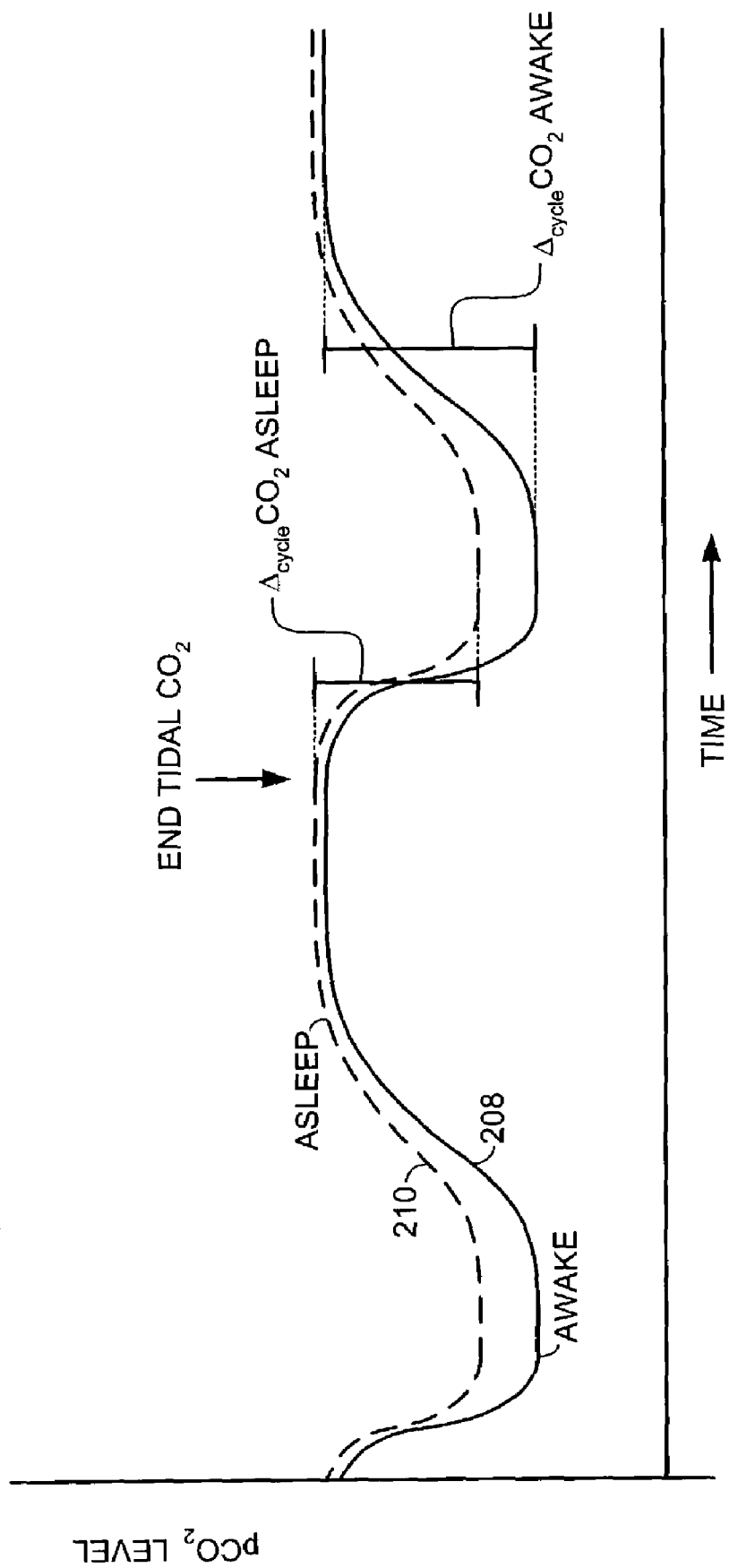
FIG. 4 is a graph illustrating an individual breathing cycle and particularly illustrating the difference between sleeping and waking $\Delta_{cycle}$CO$_2$ levels and etCO$_2$ levels.

$\Delta_{cycle}CO_2$ and etCO$_2$ are both illustrated in FIG. 4, which shows changes in pCO$_2$ levels during two consecutive breathing cycles. As can be seen, the pCO$_2$ level varies from a maximum end tidal level to a minimum level. Note that the shape of the graph provided in FIG. 4 is primarily representative of a capnographic waveform, i.e. a representation of respiration pCO$_2$ levels as detected using an external respiration monitor. The actual shape of changes in pCO$_2$ levels during a breathing cycle may differ somewhat. The capnographic waveform of FIG. 4 is provided as it illustrates the general cyclic change in pCO$_2$ levels during a breathing cycle. In any case, two separate graphs are illustrated in FIG. 4: graph 208, shown with a solid line, illustrates the change in pCO$_2$ level occurring while the patient is awake; graph 210, shown with a dashed line, illustrates the change in pCO$_2$ level while the patient is asleep. As can be seen, $\Delta_{cycle}CO_2$ while awake is greater than $\Delta_{cycle}CO_2$ while asleep. In addition, etCO$_2$ is somewhat greater while asleep, than while awake.

The $\Delta_{cycle}CO_2$ level is a greater while awake than while sleep principally because a person breathes more deeply while awake so as to increase metabolic oxygen (O$_2$) consumption. The shallower breathing that occurs while asleep results in lower metabolic O$_2$ consumption, and hence less CO$_2$ is eliminated. Accordingly, the pCO$_2$ level never reaches as low a level while asleep than while awake. EtCO$_2$ levels are generally higher while sleep than while awake because a person can tolerate a higher level of pCO$_2$ in the blood before a new inhalation is triggered. In other words, the pCO$_2$ threshold at which a new inhalation occurs is higher while asleep than while awake. Hence, both etCO$_2$ levels and $\Delta_{cycle}CO_2$ levels may be used as an indicator of the circadian state of the patient, i.e. as an indication of whether the patient is awake or asleep.

Finally, with regard to FIG. 4, waking cycle 208 and sleep cycle 210 are both shown as having the exact same frequency. In general, the frequency at which breathing occurs is generally lower while asleep than while awake. Sleeping and waking breathing cycles are shown in FIG. 4 as having the same frequency simply for clarity in illustrating the pertinent differences therebetween. In any case, regardless of any differences in the frequency of breathing, $\Delta_{cycle}CO_2$ levels are generally greater while awake than while asleep and etCO$_2$ levels are generally lower while awake than while asleep.

Returning to FIG. 3, at step 212, the detection system determines the current circadian state of the patient based upon a combination of $\Delta_{cycle}CO_2$, etCO$_2$, minute ventilation and activity levels. Finally, at step 214, the detection system adjusts pacing parameters based upon the current circadian state. For example, the current base pacing rate may be reduced while the patient is deemed to be asleep. If the pacemaker is provided with separately programmable base rates and circadian rates, the detection system controls the pacemaker to switch from the base rate to the circadian rate whenever the detection system determines the patient has transitioned from a waking state to a sleeping state. In addition to controlling pacing parameters, the detection system may control diagnostic functions of the device to, for example, trigger various self-tests of the device while the patient is asleep, since such tests are more advantageously performed while the patient is asleep due to generally lower pacing rates and correspondingly lower demands on the power supply and processing capabilities of the implanted device. In general, any of a wide variety of adjustments to the operational parameters of the implanted device may be performed, at step 214, based on the circadian state and no attempt is made herein to describe all such possible operations.

As noted, at step 212, the detection system detects the current circadian state of the patient based upon a variety of parameters that generally vary with circadian state including some combination of $\Delta_{cycle}CO_2$, $etCO_2$, minute ventilation and activity levels. In one example, the system combines the various circadian parameters together to yield a single value or "metric" representative of the current circadian state. For example, each of the individual circadian parameters may be normalized, then averaged together, to yield the metric. Of course, calculation of the metric takes into account that some parameters, such as $\Delta_{cycle}CO_2$, tend to be numerically greater while the patient is awake whereas others, such as $etCO_2$ tend to be numerically lower. Hence, the combined metric is not calculated by simply averaging raw data together. In any case, the metric is then compared against threshold values indicative of whether the patient is asleep or awake. Preferably, a running average is maintained over the last one hour of detected parameters.

In general, it is believed that $CO_2$-based parameters provide a more reliable indication of circadian state than minute ventilation or activity. Accordingly, the metric, which represents a combination of all detected circadian parameters, preferably weights the $CO_2$-based parameters (i.e. $\Delta_{cycle}CO_2$ and $etCO_2$) more heavily than minute ventilation and activity. In one specific example, the parameters associated with $CO_2$ levels are doubled as compared to the activity parameters and minute ventilation parameters prior to combining to yield the single metric. As can be appreciated, a wide variety of techniques may be employed for combining or blending the information received from various sensors into a single value that can be compared against predetermined threshold levels.

Insofar as the threshold levels are concerned, in one example, a single upper threshold is employed and, if the combined metric exceeds the upper threshold, the patient is deemed to be awake. Likewise, a single lower threshold is employed and, if the combined metric falls below the lower threshold, the patient is deemed to be asleep. If the metric falls between the upper and lower threshold values, the system considers the circadian state to be currently ambiguous and hence makes no changes to operational parameters of the device. In other implementations, a single threshold is provided and the detection system identifies the current circadian state simply based upon whether the combined metric exceeds or falls below the single threshold value. In still other implementations, different threshold values may be employed depending upon whether the patient is currently in the sleep state or the waking state. In other words, once the patient is deemed to be asleep, a higher threshold must be surpassed before the detection system concludes that the patient has awoken and resets operational parameters of the implanted device. Likewise, once the patient is deemed to be awake, the metric must fall below a lower threshold before the detection system concludes that the patient has fallen asleep. Hence, once a detection system has identified the current circadian state, it is biased to remain within that state. This helps prevent frequent changes in operational parameters of the device in circumstances where in the parameters used to detect the circadian state yield generally ambiguous results.

Figure 5:
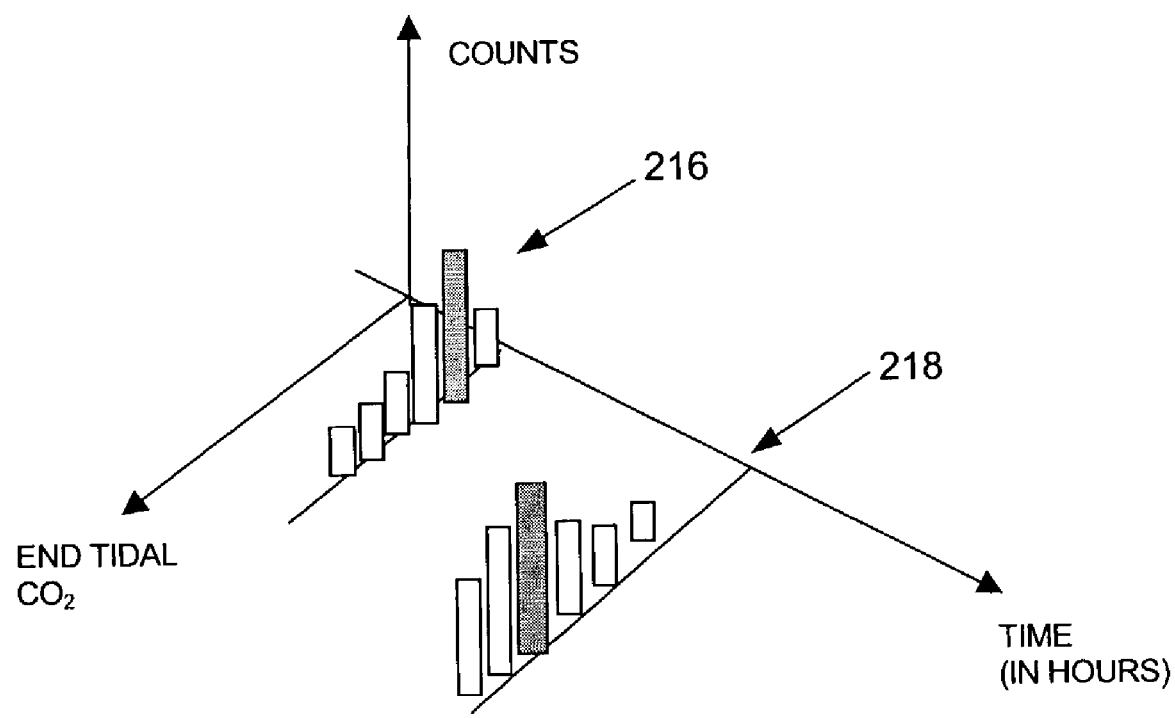
FIG. 5 is a graph illustrating a histogram employed by the circadian state detection system of FIG. 2 to determine circadian states.
Figure 6:
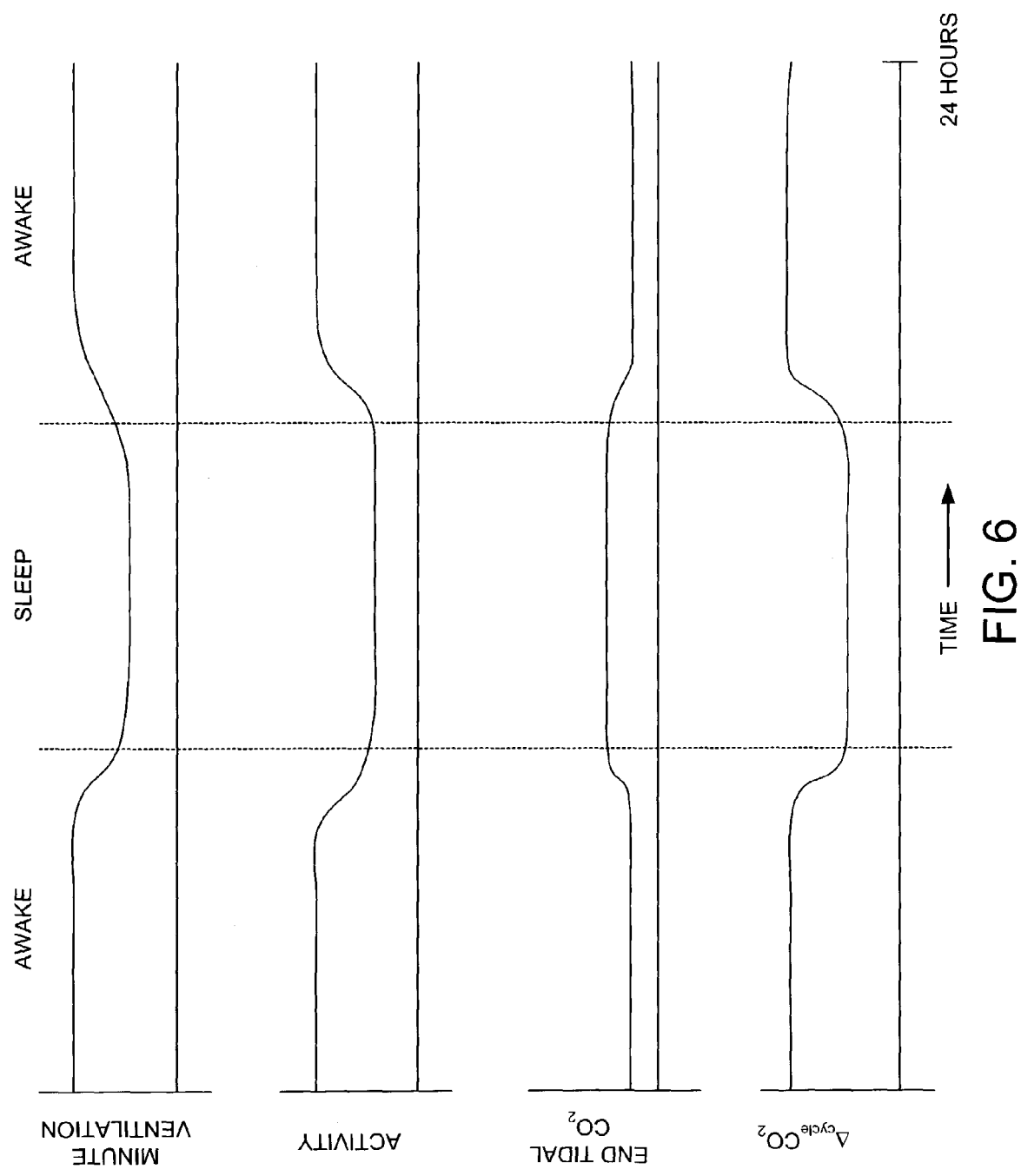
FIG. 6 is a graph illustrating changes in $\Delta_{cycle}$CO$_2$, etCO$_2$, minute ventilation and activity levels over a period of twenty-four hours as a result of circadian cycles for a healthy patient.
Figure 7:
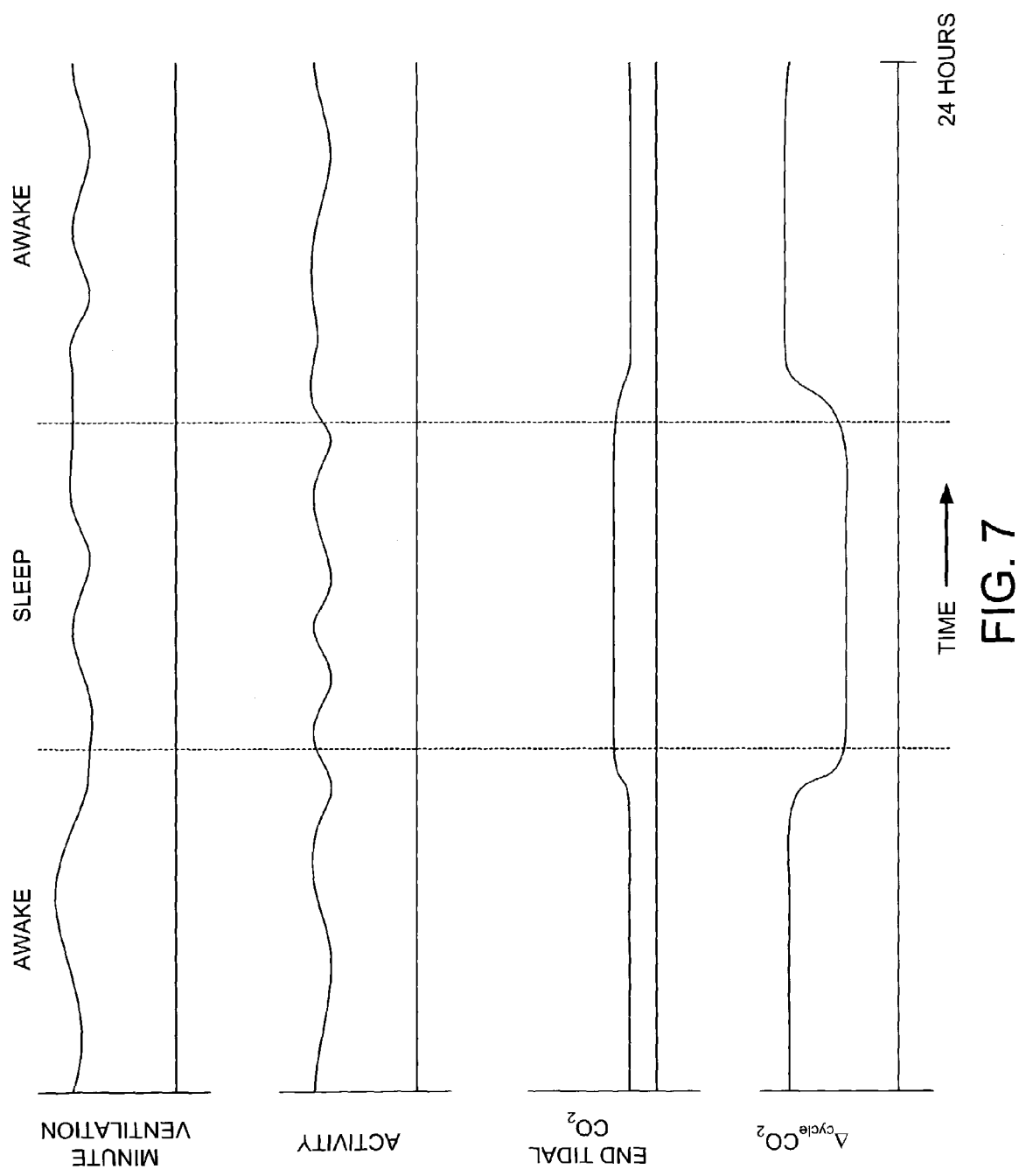
FIG. 7 is a graph illustrating changes in $\Delta_{cycle}$CO$_2$, etCO$_2$, minute ventilation and activity levels over a period of twenty-four hours for a patient with CHF.

An alternative technique for determining the circadian state, at step 212, is graphically represented in FIG. 5. The technique employs a three-dimensional histogram. In the specific example of FIG. 5, $etCO_2$ levels are detected then used to increment counters within a set of histogram bins. Each bin corresponds to a range of breath-by-breath $etCO_2$ levels. If the patient is asleep, bins indicative of relatively high $etCO_2$ levels are incremented more often than those indicative of low $etCO_2$ levels. While the patient is asleep, the opposite occurs. Periodically, preferably once each hour, the detection system examines the counter values within each of the bins and determines the current circadian state based upon the relative shape of the resulting histogram or upon some value representing the average of the histogram values. Within FIG. 5, histogram 216 illustrates exemplary counter levels occurring while the patient is awake. Histogram 218 illustrates exemplary counter levels occurring while the patient is asleep. Additional histograms may be maintained for each of the parameters that have been detected. Alternatively, the aforementioned combined metric may be used to increment bins within a metric histogram. The centroid of each one hour's worth of histogram data may be calculated to summarize the trend in data such that each full histogram need not be stored for more than one hour thus saving memory. In any case, once the shape of the bins of the latest histogram has been examined and a determination of the current circadian state is made, the bins are cleared. In still other implementations, fuzzy logic is employed to determine the current circadian state based upon relative the values of the various detected parameters.

Referring to the remaining figures, various examples will now be described. Within FIG. 6, variations in average minute ventilation, activity level, $etCO_2$ and $\Delta_{cycle}CO_2$ are shown over a period of twenty-four hours. As can be seen, while the patient is awake, minute ventilation, activity and $\Delta_{cycle}CO_2$ levels are generally higher than while asleep. $EtCO_2$ levels are generally lower while awake than while asleep. Hence, in the example FIG. 6, each of the parameters varies strongly with circadian state and any one of the parameters can be used to detect the circadian state. However, depending upon the particular patient, some of the individual parameters may vary in ways that are unexpected or ambiguous. For example, within FIG. 7, both minute ventilation and activity parameters vary generally randomly over the course of the day, perhaps as a result of labored breathing, such that circadian cycles cannot reliably be determined therefrom. However, both the $etCO_2$ and $\Delta_{cycle}CO_2$ levels vary strongly with circadian state. This is one reason why, preferably, the $CO_2$-based parameters are weighted more heavily in the determination of the circadian state than either activity or minute ventilation. In the specific example of FIG. 7, the on-going variations in minute ventilation and activity may be the result of, for example, CHF.

Figure 8:
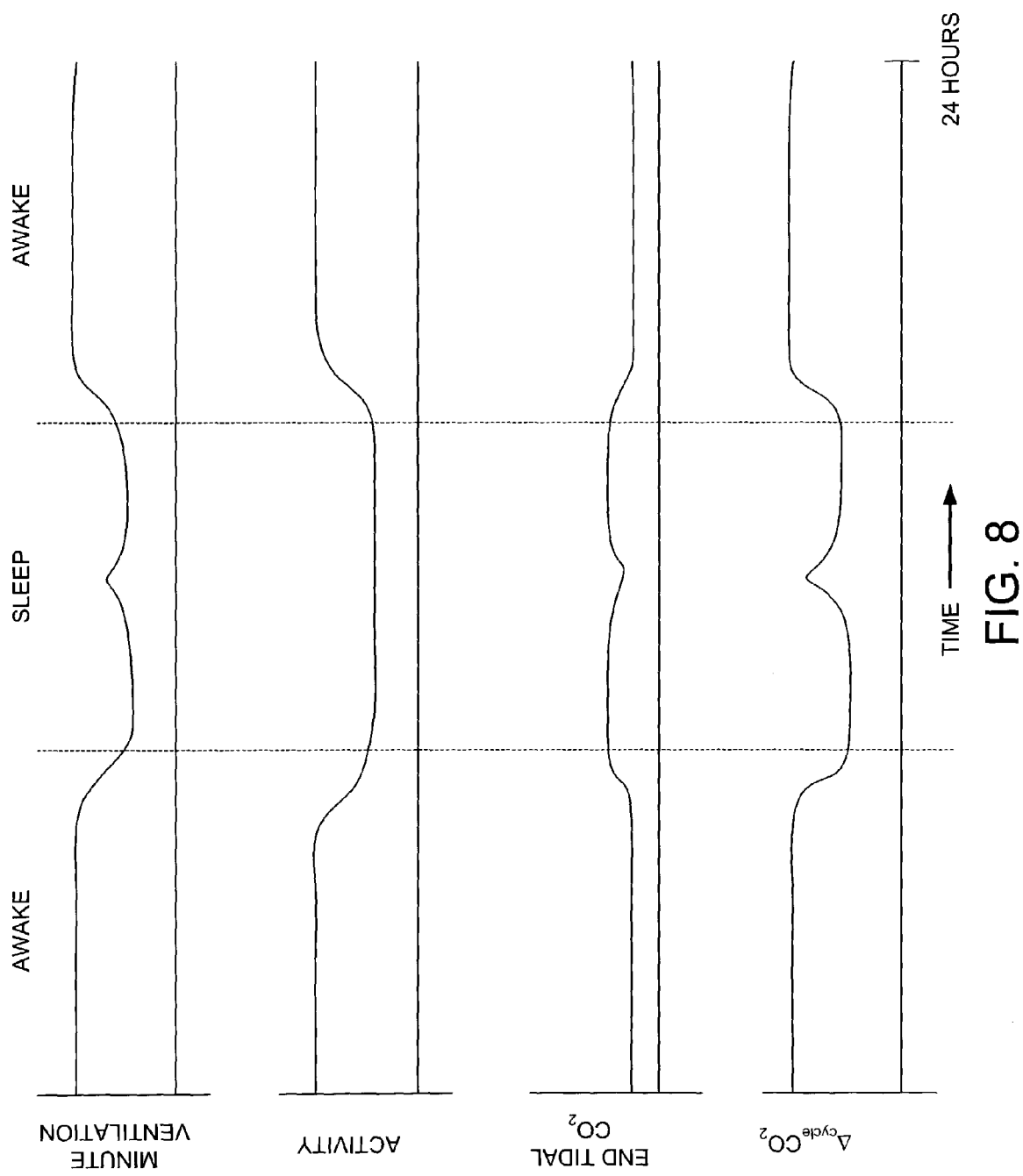
FIG. 8 is a graph illustrating changes in $\Delta_{cycle}$CO$_2$, etCO$_2$, minute ventilation and activity levels over a period of twenty-four hours for a patient who briefly awakens during the night.

FIG. 8 illustrates an example wherein a temporary change in $\Delta_{cycle}CO_2$ and $etCO_2$ levels occurs while patient is asleep. This may be the result of a period of somewhat deeper breathing while the patient is asleep. Because breathing is deeper, minute ventilation also increases temporarily. However, because patient is still asleep, activity remains at a low level. Hence, FIG. 8 illustrates the desirability of employing activity-based parameter along with the other parameters to help prevent a false detection of a change in circadian state.

If blood CO$_2$ levels only were employed, the detection system might erroneously conclude that the patient has awoken.

Figure 9:
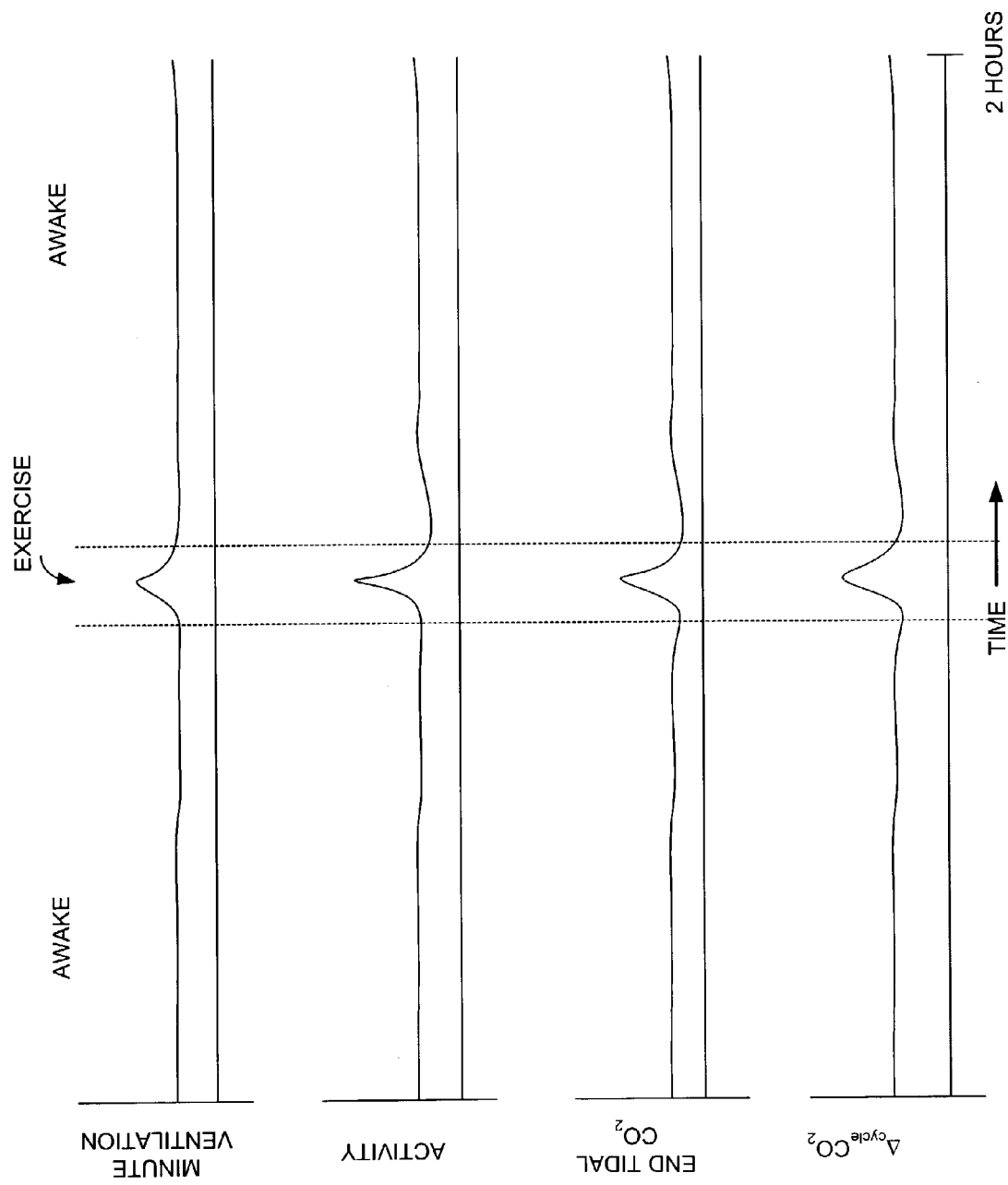
FIG. 9 is a graph illustrating changes in $\Delta_{cycle}$CO$_2$, etCO$_2$, minute ventilation and activity levels over a period of two hours while awake for a patient who briefly exercises.

FIG. 9, which covers only a period of two hours, illustrates a brief burst of exercise occurring while the patient is awake. As can be seen, minute ventilation, activity, etCO$_2$ and $\Delta_{cycle}$CO$_2$ levels all spike upwardly briefly. Hence, FIG. 9 illustrates that brief increases in etCO$_2$ levels should not be misconstrued as an indication of entry into a sleep state. By basing the detection of the circadian state on at least an hour worth of data, such misinterpretations are substantially avoided. As explained above, although exercise can raise etCO$_2$ levels temporarily, most patients with pacemakers or ICDs do not engage in enough exercise to elevate the average etCO$_2$ level while awake over the average etCO$_2$ level while asleep. Moreover, by factoring in activity and minute ventilation into the circadian state detection, false detections of sleep states are further avoided.

Figure 10:
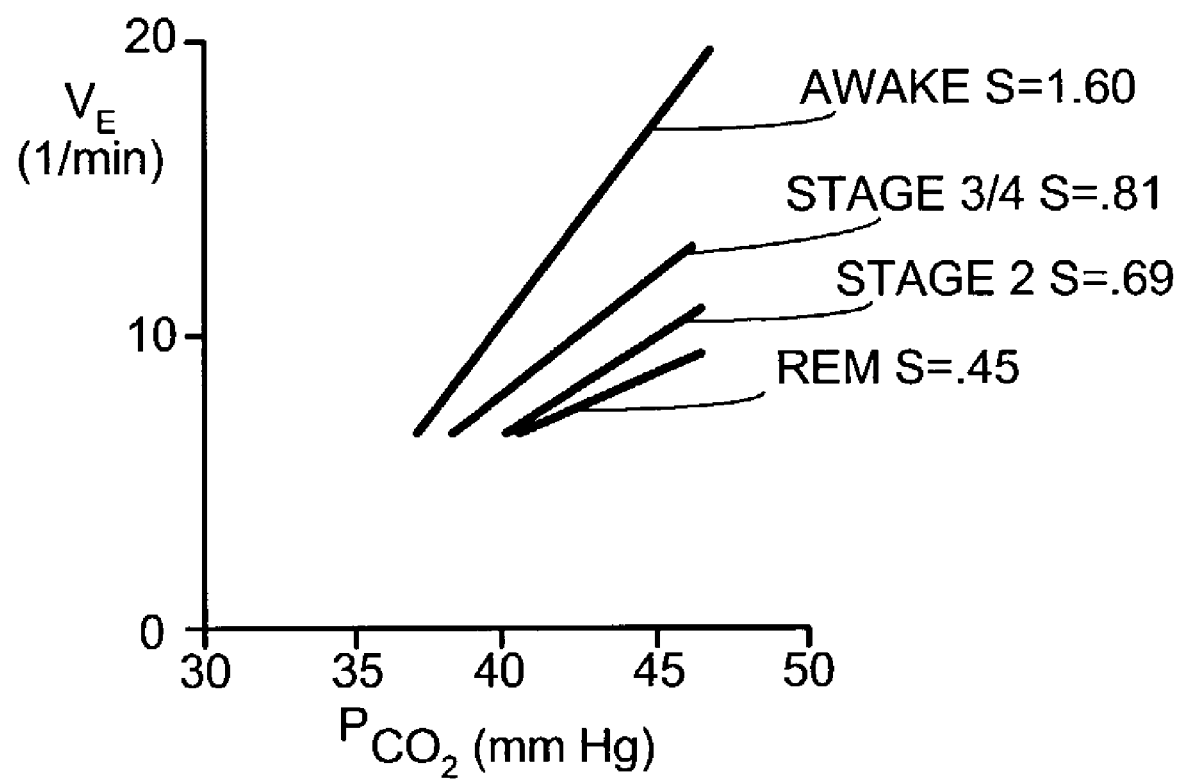
FIG. 10 is a graph illustrating minute ventilation vs. pCO$_2$ for various stages of sleep.

Additionally, it has been found that blood CO$_2$ levels vary according to the stage of sleep. This is illustrated in FIG. 10, which shows minute ventilation values ($V_E$) as a function of pCO$_2$ levels for various sleep stages. As can be seen from the figure, the pCO$_2$ triggering point at which inhalation begins is lowest while awake, higher while in stage 3/4 sleep, still higher in stage 2 sleep, and highest in rapid-eye movement (REM) sleep. Since etCO$_2$ levels depend upon the pCO$_2$ concentration that triggers inhalation, etCO$_2$ levels likewise depend on the stage of sleep and so changes in etCO$_2$ levels while asleep can be used to detect the sleep stage. Also, note that the slope of minute ventilation as a function of pCO$_2$ varies according to sleep state, with the slope equal to 1.60 while awake, 0.81 while in stage 3/4 sleep, 0.69 while in stage 2 sleep and 0.45 while in REM sleep. Thus, implantable medical devices such as devices incorporating both chest impedance measuring devices and blood pH sensors can be configured to calculate the ratio or slope of minute ventilation to pCO$_2$ and to use the ratio to determine whether the patient is asleep or awake and, if asleep, to further determine the stage of sleep.

Figure 11:
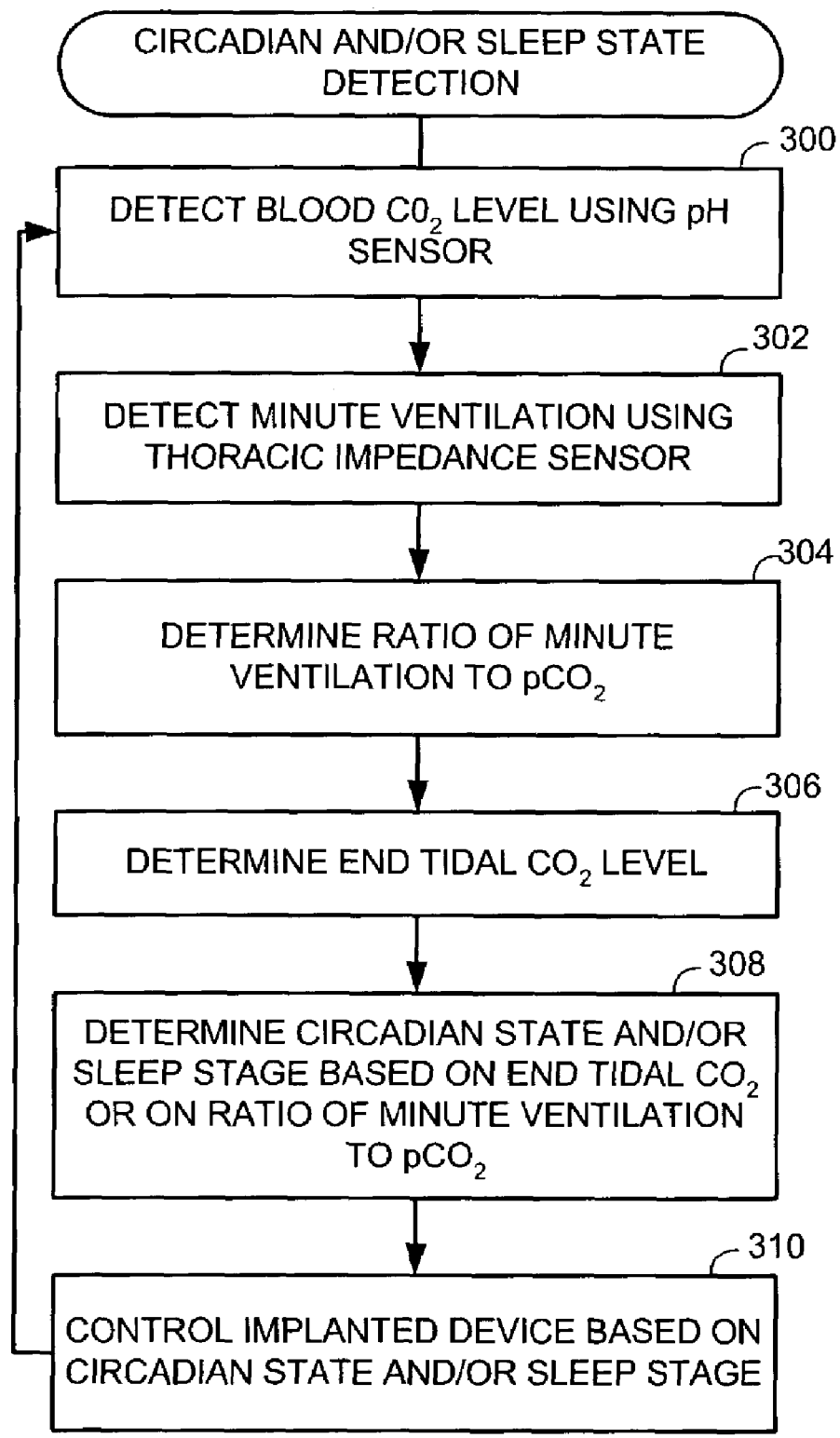
FIG. 11 is a flow diagram illustrating an alternative method performed by the circadian state detection system of FIG. 2 to determine sleep stage as well as circadian state.

An exemplary technique for detecting circadian state and/or sleep stage based on the ratio of minute ventilation to pCO$_2$ is shown in FIG. 11. At steps 300 and 302, detection system 101 (FIG. 2) determines pCO$_2$ and minute ventilation based on signals received, respectively, from the pH/CO$_2$ sensor and the minute ventilation sensor (also FIG. 2.) At step 304, the detection system determines the ratio or slope of minute ventilation to pCO$_2$. This may be determined, for example, by averaging pCO$_2$ levels and minute ventilation levels over some period of time (such as the last fifteen minutes) then taking the numerical ratio of the two averaged values or by recording individual pairs of values of minute ventilation and pCO$_2$ and determining the slope. In any case, at step 306, the detection system also determines the average etCO$_2$ level (or end tidal pH level). Then, at step 308, the detection system determines the circadian state of the patient based upon either the average etCO$_2$ level or the average ratio of minute ventilation to pCO$_2$ or a combination of both. If the patient is asleep, the detection system further determines the stage of sleep, i.e. either REM, stage 2 or stage 3/4. Finally, at step 310, the detection system adjusts control parameters of the implanted device based upon the current circadian state and/or the current sleep stage.

For example, if the ratio of minute ventilation to pCO$_2$ is found, at step 308, to be greater than 1.0, the patient is deemed to be awake; otherwise, the patient is deemed to be asleep. If the ratio is found to be in the range of 0.75 to 1.0, the patient is deemed to be in stage 3/4 sleep. If the ratio is found to be in the range of 0.50 to 0.75, the patient is deemed to be in stage 2 sleep. If the ratio is found to be less than 0.50, the patient is deemed to be in REM sleep. These thresholds may be calibrated for use with particular patients. Likewise, the average etCO$_2$ level can be compared against threshold values to determine the stage of sleep, with the appropriate threshold levels determined experimentally and calibrated, if needed, for use with particular patients. A metric can be generated that combines the ratio data and the etCO$_2$ data to determine the circadian state and/or sleep stage, with the ratio data and the etCO$_2$ data weighted relative to one another, as desired. Moreover, the ratio data can also be used to supplement the circadian state detection technique of FIG. 3., i.e. it can be combined with activity data, $\Delta_{cycle}$CO$_2$ data, etc.

Hence, analysis of blood CO$_2$ alone or in combination with minute ventilation may be used to distinguish stages of sleep and, if desired, operational parameters of the implantable medical device may be adjusted based upon sleep state. Although the examples provided herein primarily relate to implantable cardiac stimulation devices, principles of the invention may be employed within other implantable medical devices, such as neurostimulation devices, wherein the operation of the device may need to be controlled based upon the sleep state of the patient. The techniques invention are applicable in a wide variety of applications and no attempt made herein to enumerate all such applications.

What have been described are various techniques performed by an implantable cardiac stimulation device primarily for detecting circadian state and for controlling functions of the device in view of the circadian state. However, principles of the invention may be exploiting using other implantable medical devices. In addition, while the invention has been described with reference to particular embodiments, modifications can be made thereto without departing from the spirit and scope of the invention.

What is claimed is:

1. In an implantable medical device for implant within a patient, a method for detecting a circadian state of the patient, the method comprising:

detecting changes in one or more blood carbon dioxide (CO$_2$) parameters;

determining the circadian state of the patient based upon the changes in the one or more blood CO$_2$ parameters;

detecting minute ventilation levels of the patient and wherein the step of determining the circadian state of the patient additionally takes into account the detected minute ventilation levels;

determining a ratio of minute ventilation to blood CO$_2$ levels of the patient and wherein the step of determining the circadian state of the patient additionally takes into account the determined ratio; and detecting activity levels of the patient;

wherein detecting changes in selected blood CO$_2$ parameters is performed to detect changes in etCO$_2$ levels and changes in $\Delta_{cycle}$CO$_2$; and wherein the step of determining the circadian state of the patient takes into account a combination of $\Delta_{cycle}$CO$_2$ levels, etCO$_2$ levels, activity levels and minute ventilation levels.

2. The method of claim 1 wherein detecting changes in selected blood CO$_2$ parameters comprises detecting changes in maximum variation of pCO$_2$ level per breathing cycle ($\Delta_{cycle}$CO$_2$).

3. The method of claim 1 wherein detecting changes in selected blood $CO_2$ parameters comprises detecting changes in maximum variation of blood pH level per breathing cycle ($\Delta_{cycle}pH$).

4. The method of claim 1 wherein determining the circadian state of the patient based upon the changes in the selected blood $CO_2$ parameters comprises identifying whether the patient is asleep or awake.

5. The method of claim 1 further comprising determining a sleep stage of the patient based on the ratio of minute ventilation to blood $CO_2$ levels of the patient.

6. The method of claim 1 further comprising controlling device functions based on the detected circadian state of the patient.

7. In an implantable medical device for implant within a patient, a method for detecting a circadian state of the patient, the method comprising:
   detecting changes in one or more blood carbon dioxide ($CO_2$) parameters to detect changes in $etCO_2$ levels and changes in $\Delta_{cycle}CO_2$ levels;
   determining minute ventilation levels of the patient;
   detecting activity levels of the patient; and
   determining the circadian state of the patient comprising:
   generating histograms representative of a range of values of the $etCO_2$ levels, $\Delta_{cycle}CO_2$ levels, activity levels, and minute ventilation levels detected over a period of time; and
   identifying the circadian state of the patient based upon the shape of the histograms.

8. In an implantable medical device for implant within a patient, a control system comprising:
   a blood $CO_2$ sensor detecting changes in $etCO_2$ levels and changes in $\Delta_{cycle}CO_2$;
   an activity sensor detecting activity levels of the patient;
   a minute ventilation sensor detecting minute ventilation levels of the patient; and
   a controller operative to control device functions based on a combination of $\Delta_{cycle}CO_2$ levels, $etCO_2$ levels, activity levels and minute ventilation levels;
   wherein the controller determines a circadian state of the patient by taking into account a combination of $\Delta_{cycle}CO_2$ levels, $etCO_2$ levels, activity levels and minute ventilation levels.

9. In an implantable medical device for implant within a patient, a method for detecting a circadian state of the patient comprising:
   detecting blood carbon dioxide levels ($pCO_2$) to detect changes in $etCO_2$ levels and changes in $\Delta_{cycle}CO_2$;
   detecting minute ventilation levels;
   detecting activity levels; and
   determining the circadian state of the patient based upon a combination of $\Delta_{cycle}CO_2$ levels, $etCO_2$ levels, activity levels and minute ventilation levels.

10. The method of claim 9 further comprising determining a sleep stage of the patient based on the ratio of minute ventilation to blood $CO_2$ levels of the patient.

* * * * *